(12) United States Patent
Woudstra et al.

(10) Patent No.: US 10,195,460 B2
(45) Date of Patent: Feb. 5, 2019

(54) SYSTEM AND METHOD FOR PERFORMING BRACHYTHERAPY

(71) Applicant: Nucletron Operations B.V., Veenendaal (NL)

(72) Inventors: Bas Woudstra, Veenendaal (NL); Johan Henning, Veenendaal (NL)

(73) Assignee: Nucletron Operations B.V., Veenendaal (NL)

( * ) Notice: Subject to any disclaimer, the term of this patent is extended or adjusted under 35 U.S.C. 154(b) by 310 days.

(21) Appl. No.: 15/158,564

(22) Filed: May 18, 2016

(65) Prior Publication Data

US 2016/0339267 A1    Nov. 24, 2016

(30) Foreign Application Priority Data

May 19, 2015    (NL) .................................... 2014824

(51) Int. Cl.
*A61N 5/00*    (2006.01)
*A61N 5/10*    (2006.01)
*A61B 90/98*    (2016.01)

(52) U.S. Cl.
CPC ............ *A61N 5/1007* (2013.01); *A61B 90/98* (2016.02); *A61N 5/1049* (2013.01); *A61N 5/1075* (2013.01); *A61N 2005/1008* (2013.01); *A61N 2005/1051* (2013.01)

(58) Field of Classification Search
CPC .. A61N 5/1001; A61N 5/1007; A61N 5/1008; A61N 5/1048; A61N 5/1049; A61B 90/98
USPC .......................................................... 600/1–8
See application file for complete search history.

(56) References Cited

U.S. PATENT DOCUMENTS

| 5,800,333 | A | 9/1998 | Liprie |
| 5,851,172 | A | 12/1998 | Bueche et al. |
| 2008/0165058 | A1* | 7/2008 | Ayachitula ............ G01S 7/4021 342/359 |
| 2012/0215052 | A1* | 8/2012 | Kindlein ............... A61N 5/1007 600/4 |

(Continued)

FOREIGN PATENT DOCUMENTS

WO    WO 2006/067377 A1    6/2006

*Primary Examiner* — John Lacyk
(74) *Attorney, Agent, or Firm* — Finnegan, Henderson, Farabow, Garrett & Dunner LLP

(57) ABSTRACT

A system for transporting a source for brachytherapy may include a source guide, a detector, and a controller. The source guide may be configured to guide a source transport for transporting the source, wherein the source guide includes at least one electronic tag. The detector may be configured to detect a frequency signal generated by the at least one electronic tag, wherein the frequency signal varies when the source transport is proximate to the at least one electronic tag. The controller may be configured to receive the frequency signal from the detector and determine a path of the source transport based on the frequency signal. A method for transporting a source used for brachytherapy may include detecting a frequency signal generated by at least one electronic tag associated with a source guide configured to guide a source transport for transporting the source. The frequency may vary when the source transport is proximate to the at least one electronic tag. The method may further include determining a path of the source transport based on the frequency signal.

22 Claims, 6 Drawing Sheets

(56) References Cited

U.S. PATENT DOCUMENTS

2016/0166328 A1\* 6/2016 De Vries .............. A61N 5/1039
600/424

\* cited by examiner

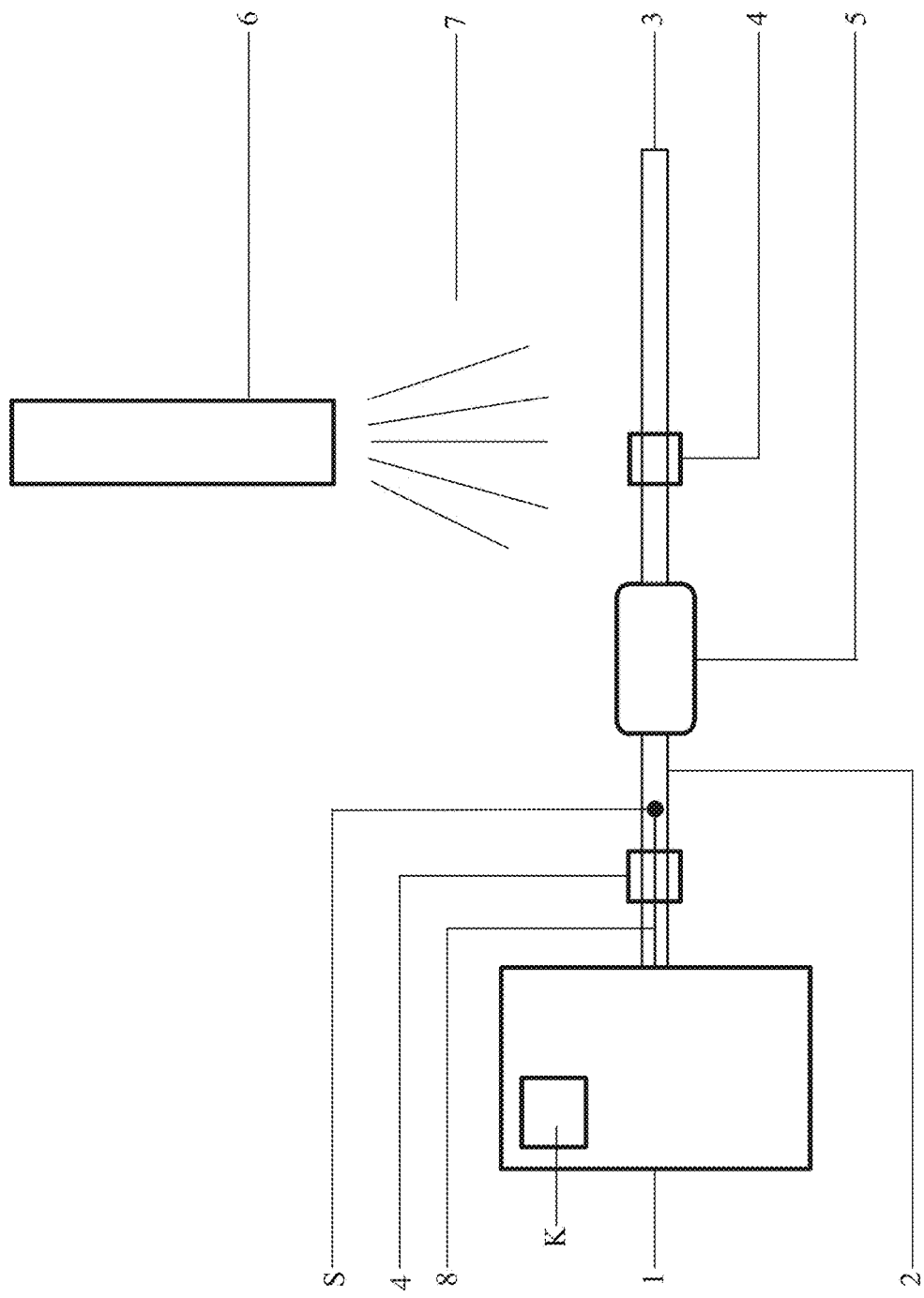

SYSTEM AND METHOD FOR PERFORMING BRACHYTHERAPY

PRIORITY

This patent application claims the benefit of priority under 35 U.S.C. § 119 to Netherlands Patent Application No. 2014824, filed on May 19, 2015, which is incorporated herein by reference in its entirety.

TECHNICAL FIELD

This disclosure relates to a system for performing brachytherapy and method for guiding a transport means through a source guide

BACKGROUND

The use of electronic tags in brachytherapy is described in WO 2006/067377 ("WO'377"). WO'377 describes an apparatus and a method to track and identify radioactive sources by
coupling a first end of a guide tube to a first housing for a radioactive source and a second end of the guide tube to a second housing for the radioactive source; and
identifying the coupling of the guide tube to one or both of the first housing and the second housing with one or more electronic tags disposed on at least one of the guide tube, first housing, and second housing to communicate identification information.

A problem with WO'377 is that the RFID-tags only provide information on the status of the coupling between the various devices in the system. As such, it may still be conceivable that a source is erroneously introduced into the wrong catheter.

SUMMARY

Certain embodiments of the present disclosure aim to improve the known systems and methods, particularly to solve or alleviate the above-mentioned problems.

In an exemplary embodiment, the present disclosure is directed to a system for providing brachytherapy, including at least one source guide configured for guiding a transport means, characterised in that the source guide includes at least one electronic tag configured to provide identification information, wherein the electronic tag is configured to cooperate with the transport means, when the transport means passes the electronic tag.

In this way, accuracy of positioning of, for example, a source can be improved. Also, the risk of using a wrong channel can be reduced or removed.

The system can increase the safety of brachytherapy. As a transport means, consisting of, for example, a flexible wire, such as a flexible metal guidewire, passes the electronic tag, the electronic tag can provide identification information, which can be used to confirm that the proper transfer tube or guiding tube is provided with the radioactive source. Subsequently, the system is faster to use than conventional systems. Using one or more electronic tags, it becomes possible to quickly detect whether the proper channel, transfer tube, applicator and/or applicator connection is used. The transfer tube may herein also be a catheter or flexible tube, for example made of a plastic.

It should be noted that the term "source guide" should be interpreted broadly. The source guide can be configured to guide a source or an element including or being connected to a source, for example a radioactive source. The source guide can be an applicator, a transfer tube, a needle, or a different type of guiding means.

It should be observed that the transport means may actually hold a radioactive source (emitting radiation), but that is not required. For example, according to an embodiment, the transport means may be a check-cable (e.g., to be used in verifying proper functioning of the system before treatment), a dummy source, EM cable, radioactive source etc.

In an example, the electronic tag includes an electronic circuit having a coil that encloses a source guide path, through which said transport means passes.

In an embodiment the electronic tag is a passive electronic tag, for example an RFID-tag (Radio Frequency IDentification tag) or EM-tag (ElectroMagnetic tag), that is configured to absorb part of a broadband radiofrequency signal at a specific frequency. The advantage of a passive electronic tag is that no power source needs be attached to operate the tag. This reduces the risk of failure or malfunction.

In an example, the specific frequency is a resonance frequency of an LC-circuit, formed in part by the coil.

In a further example, the resonance frequency of an electronic tag is a unique resonance frequency. For example the tag can be trimmed to such a frequency using laser-trimming.

The advantage of the electronic tag having a unique resonance frequency is that identification of a particular electronic tag can be executed, even if multiple electronic tags are used in one system. In addition, each electronic tag can be assigned a channel number that can be visualised on the outside of the electronic tag. It should be observed that the electronic tag can be provided with a unique resonance frequency in a various ways, as will be appreciated by the skilled person.

Furthermore, in some embodiments, the resonance frequency depends on a presence of a radioactive source transport means in or near the tag. As is mentioned before, the term "radioactive source transport means" should be interpreted broadly since it may also include a source transport means that does not actually hold a radioactive (e.g., a check cable, dummy cable).

When a radioactive source transport means is guided near or into the tag, this causes a change in coil inductance (in an inductive system) or a change in capacitance (capacitive system). As a result, the resonance frequency of the electronic tag will detune slightly (e.g., providing a resonance frequency that is higher or lower than the resonance frequency without the transport means near or in the electronic tag).

According to a further embodiment, the system includes a detector, particularly a tag-reader, configured for detecting the electronic tag. The use of a detector enables the detection and monitoring of an electronic tag to receive identification information sent by the electronic tag. The detector may also be configured to be auto-calibrating in that it, in the absence of a transport means near or in the electronic tag, can measure and store the resonance frequency of the electronic tag as nominal frequency, thus calibrating the detector to the resonance frequency of the electronic tag. The auto-calibration option provides the advantage that the system can be used in a wide range of environmental conditions, auto-calibrating it for the conditions on or in that specific location. In addition, the auto-calibrating option can also be used to test the system for errors or malfunctioning before and/or during and/or after use. This provides an extra safeguard and, thus, increases security for the users. In addition, regular auto-calibration also provides insight into the performance of the system, which can be used to (further) optimize the system. Also, the auto-calibration may be used to detect available tags that are connected to the system. The frequency bandwidth of the electromagnetic field transmitter is then automatically adapted to include only the frequency bandwidth of the detected tags. As a result, the detection speed of the system is increased.

In another embodiment, the detector is integrated in an afterloader suited for delivering a radioactive source to a transfer tube. This provides the advantage that no additional electronic tag reader needs to be placed in the area where the treatment is to be administered.

According to a further embodiment, the system may also include a visualisation means, for example connected to the detector, for visualising the signals or related information, based on detection via the electronic tag.

In some embodiments, detection via the tag is used to verify a movement or position of said transport means.

Besides, in some embodiments, the tag as such can be used to provide a reference or reference point, for example, indicating a start of a further path for the transport means or respective source (e.g., towards a desired treatment and/or target position, particularly a distal dwelling position). In this way, accurate source positioning and improved treatment can be achieved.

The system can include a controller (e.g. processor) configured to carry out such a verification and/or reference point determination. For example, the controller can be configured to process data relating to tag detection by the detector, and to verify if a detection by a tag (i.e. based on a said cooperation with a source transport means) corresponds to a desired or programmed path for that source transport means. Also, the controller can be configured to use a detected tag position as a reference, indicating a start of a further path for the transport means or respective source (towards a desired treatment/dwelling position).

In some embodiments, the controller can be configured to adjust positioning of the source transport means, based on a detected reference or reference point as indicated by detection of a respective tag. For example, the controller can be configured to position the transport means, based on a predetermined treatment plan (e.g. provided by treatment planning software), wherein a position of a tag is used to set a starting position along a source trajectory (the starting position being remote from one or more distal, desired source treatment positions). Then, the controller can accurately control source movement (i.e. positioning a source at a desired treatment position) taking into account a detected position of the tag during operation.

In an embodiment, the controller can also be configured to generate an alarm signal in case a detection by a tag does not corresponds to the desired or programmed path for that source transport means, for example, in case it is found that a source enters another channel than the expected channel. In that case, the controller can be configured to halt a further movement of the source transport means, preferably immediately retracting the transport means into the applicator, in case it finds that a detection by a tag does not corresponds to the desired or programmed path for that source transport means.

The frequency can detune as a transport means passes through the electronic tag, which information can be used as a remote sensor to identify the location of the radioactive source transport means.

The system may include an embodiment in which at least part of the electronic tag is visible. Also, in a preferred embodiment the tag can include a detectable identification code, for example text, a printed pattern and/or colour code.

According to an embodiment, the system may include an electronic tag in which the tag is integrated in a closed housing suitable for sterilisation purposes. The advantage of a (preferably hermetically sealed) closed housing is that the electronic tag is substantially impervious to outside influences. Having a housing suitable for sterilisation particularly means that an outside of the housing, which may be in contact with a patient during treatment, may be sterilised using (standard) sterilisation equipment. As a result, the electronic tag can be re-usable, and can also relatively quickly be prepared for re-use after it has been used in a treatment.

Also, according to an embodiment, the tag can be supplied separately, so that the tag can be placed on e.g. an applicator or other source guide. For example, the coupling of the tag to the guide can be achieved using a clicking or clamping fixation.

In an embodiment, the electronic tag is attached to a source guide (e.g., using a clamp or clip), such as a cable, a needle or an applicator. Adding an attaching means to the electronic tag allows easy connection of the electronic tag with the source guide. In addition, it allows the electronic tag to be used on existing applicators, which increases the scope of use.

The electronic tag can also be an integral part of the source guide. In such an embodiment, the source guide may be configured to contain an electronic tag. A source guide with integrated electronic tag has several advantages. First of all, integration allows for a plug-and-play mode, for no additional actions need to be taken to attach it. Moreover, being integrated in a fixed position, the electronic tag is inherently placed in the right position on the source guide. Also, the electronic tag can provide information on the (type of) source guide. This, for example, includes the addition of a small ferrite pallet in the source guide to uniquely identify for example the cable type (e.g., small, medium, large).

According to another embodiment, the system is provided with multiple source guides configured for conducting source transport means, wherein each source guide is provided with at least one electronic tag configured to provide identification information, wherein the identification information provided by each electronic tag is preferably unique. In a system with multiple electronic tags, each providing unique identification information, it may also be advantageous to provide special tags (or frequencies) to detect specific elements of the system, such as for example a transport container or a source positioning ruler. Furthermore, the system according to this aspect of the disclosure may be adapted to a plug-and-play system. In such system, the system detects which selector channels are used by detecting which transfer tubes are connected. During a test run, the transport means without a radioactive source is provided into the multiple channels. The system detects the connections between the various applicator channels and the corresponding afterloader channels. The information is then used to deliver the correct positions for that channel.

The disclosure also relates to a method for guiding a transport means through a source guide, for performing brachytherapy, the method including at least one electronic tag of a source guide providing identification information, wherein the electronic tag cooperates with the transport means to provide the identification information.

In an example, the method includes de-tuning a resonance frequency of the electronic tag by the transport means.

According to an aspect of the disclosure, the method may include detecting identification information from the electronic tag by a detector, more specifically a tag-reader.

In an example, the method might include visualising said identification information, and/or information that is associated with that identification information, on said visualisation means.

According to an aspect of the disclosure, the method comprises using a source guide containing an integrated electronic tag (e.g. RFID tag or EM tag) for providing identification signals.

According to another aspect of the disclosure, the system is provided with multiple source guides configured for guiding transport means, wherein each source guide is provided with an electronic tag configured to provide identification information, wherein the identification information provided by each electronic tag is unique, the method comprising detecting the identification information from said multiple source guides.

BRIEF DESCRIPTION OF THE FIGURES

FIG. 1 is an example schematic view of a brachytherapy system, consistent with disclosed embodiments

FIG. 2c is an example cross-section along line II-II of FIG. 2a;

DETAILED DESCRIPTION

Figure 2A:
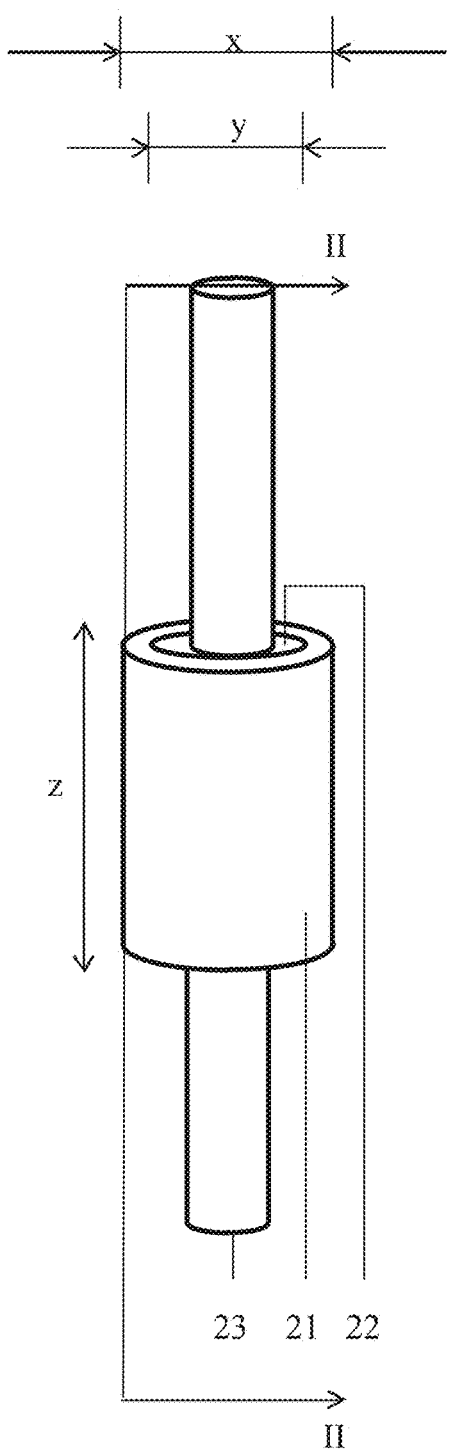
FIG. 2a is an example perspective view of a source guide with an electronic tag, of the system shown in FIG. 1.

In this application similar or corresponding features are denoted by similar or corresponding reference designators.

FIG. 1 shows a schematic view of a brachytherapy system containing one or more electronic tags, for example a Radio-Frequency Identification-tag (RFID-tag) or EM-tag. As shown in FIG. 1, the brachytherapy system is comprised of an afterloader 1 and respective controller K, a first source guide (in this example a transfer tube 2), a transfer tube-applicator coupling 5, a second source guide in the form of a brachytherapy applicator 3, electronic tags 4, a detector 6 and a transport means 8, in this example carrying a capsule containing a source S. In other embodiments, the system may include a plurality of said first source guides (transfer tubes 2), which may be associated with or connected to a plurality of afterloader channels.

As shown in FIG. 1, the afterloader 1 is connected to a first (proximal) end of at least one transfer tube 2, which may be configured for delivery of a transport means 8. The transport means 8 may, for example, include a capsule holding a radioactive source S, such that a Brachytherapy source for irradiating tissue, for example for treating a patient, or a dummy source. In case of a radioactive source S, the capsule containing the source S may be firmly fixed to the source transport means 8.

A said Brachytherapy source for irradiating tissue can comprise, for example, Cobalt-60, Cesium-137 or Iridium-192, as will be clear to the person skilled in the art. In terms of radiation activity, the source may be a high dose rate (HDR) source, a medium dose rate (MRD) source, or a low dose rate (LDR) source. Also a combination of the two types of sources is contemplated. Definitions of the HDR and the LDR sources may be found in the so-called ICRU reports (e.g., see ICRU-38, or ICRU-58).

In case of a dummy source S, a distal part of the transport means 8 may function as the dummy source. For example, the transport means 8 can be a check-cable that does not include or hold a radiation emitting source S. On the other hand, transport means 8 may include or hold a dummy source, such as an object that resembles a said radiation emitting Brachytherapy source, but that does not irradiate. The non-radiation-emitting check cable or dummy source cable can be used for example in performing a pre-treatment check of the system.

The afterloader 1 may be an afterloading device known to a person skilled in the art. The afterloader 1 may be any afterloader configured to deliver one or more radioactive sources to an applicator or catheter. This may, for example, be any of the afterloaders disclosed in U.S. Pat. No. 5,800,333, U.S. Pat. No. 5,851,172 or any other suitable afterloader. In some embodiments, the afterloader may contain a plurality of connection points (e.g. associated with one or more radiation source exit openings) for connecting catheters and/or an applicator. In other embodiments, the afterloader may be configured to deliver multiple radioactive sources. The afterloader 1 may include one or more radiation-emitting radioactive sources. Generally, a radiation vault may be included in the afterloader 1 to safely store the source(s) when the source(s) is/are not used in treating a patient.

In some embodiments, the afterloader may be configured (under control by a respective controller K) to move at least part of the transport means 8 out of a housing of the afterloader 1, feeding the transport means 8 into and through the one or more first source guides 2 and an applicator 3 (e.g., a source guide) to transport a source (or source capsule) S towards tissue to be treated. In some examples, movement of the transport means 8 with respect to the afterloader 1 may follow a pre-determined sequence, for example to carry out a certain treatment plan (generated e.g. by treatment planning software) that may, for example, be stored in a memory of the controller K.

The transfer tube 2 may be a catheter or a flexible tube, for example made of plastic, having the first side connected to an exit port of the afterloader 1 and a second side, which is opposite from said first side, connected to a first side of a transfer tube-applicator coupling 5. The transfer tube-applicator coupling 5 may enable an unimpeded transfer of the transport means 8 from the transfer tube 2 connected to its first side, to another device, in this example an applicator 3, connected on a second side, which is opposite said first side.

In some examples, the transfer tube 2 may include an electronic tag 4.

Each electronic tag 4 can be located at various locations. According to one embodiment, the tag 4 can be located at or near a proximate end (e.g. connected to the applicator 1 during operation of the system) or an opposite distal end of the respective source guide 2 and/or applicator 3. Also, according to an embodiment, the tag 4 can be located at a position remote from the opposite ends of the respective source guide 2 and/or applicator 3. According to an embodiment, a source guide 2 and/or applicator 3 can include only a single tag 4. Alternatively, two or more electronic tags 4 can be provided on/in a single source guide and applicator, preferably spaced apart from each other. In a further embodiment, the source guide can be provided with an array of tags 4.

Various types of applicators 3 can be used. For example, the applicator 3 can be an applicator used for brachytherapy treatment, for example a cervical or intravascular applicator, which may be configured with at least one respective integrated source guide to guide the transport means 8 in/along the applicator. The applicator source guide may also be provided with an electronic tag 4, which, for example, may be applied by sliding it over the applicator source guide end.

In some examples, the electronic tag 4 may be attached to the applicator source guide (e.g., using a clip or clamp). The example clip or clamp may form an integral part of the electronic tag 4, but can also be a separately configured to attach the electronic tag 4 to the source guide. In addition, the attachment may consist of two cooperating parts, one of which is connected to the electronic tag 4 and the other to a source guide.

Furthermore, the system may comprise a detector 6 (e.g., an electromagnetic field generator) configured to send and receive electromagnetic signals 7 in a predetermined bandwidth. Communicatively connected to the detector 6 can be a controller K for processing data related to detecting a said tag. In this example, the detector 6 may also comprise a signal converter that converts the electromagnetic signals 7 to information suitable to be processed by said controller K (e.g. digital information)

As shown in FIG. 1, an afterloader controller K has been schematically depicted as being part of the afterloader 1 itself. Such a controller K can also be partly or fully located remotely from the afterloader 1. It can include a microcontroller, computer, computer system, micro-electronics, and/or hardware and respective software, configured, for example, to control the afterloader 1. Afterloader control can be configured to move a said transport means 8 out of and into a housing of the afterloader 8, control such movement, verify the movement, carry out a certain treatment plan (e.g. provided by a treatment planning system), and/or other afterloader control operations as will be appreciated by the skilled person.

According to a further embodiment, an afterloader controller K can be configured to use or process information regarding a detected cooperation between a tag 4 and a transport means 8 to verify if correct connections are made between the various parts of the system (e.g., whether the correct transfer tube(s) have been connected to a certain channel of the applicator, and/or whether the correct applicator/container/calibration jig/SDS/SPCR has been connected to the correct transfer tube).

In addition or alternatively, the afterloader controller K can be configured to use or process information regarding a detected cooperation between a tag 4 and a transport means 8 to fine-tune transport means positioning.

Figure 2B:
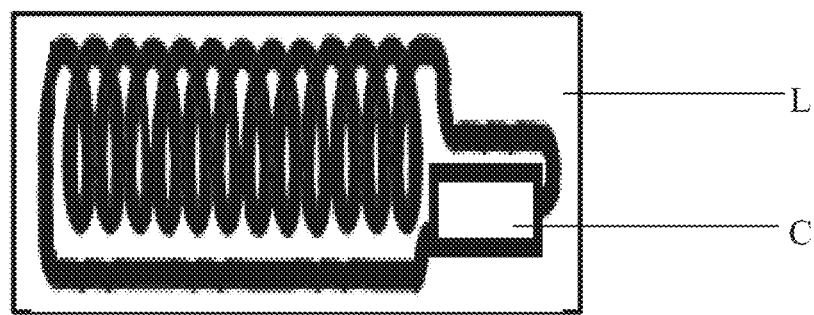
FIG. 2b is a schematic view of an example of the electronic tag, consistent with disclosed embodiments.
Figure 2C:
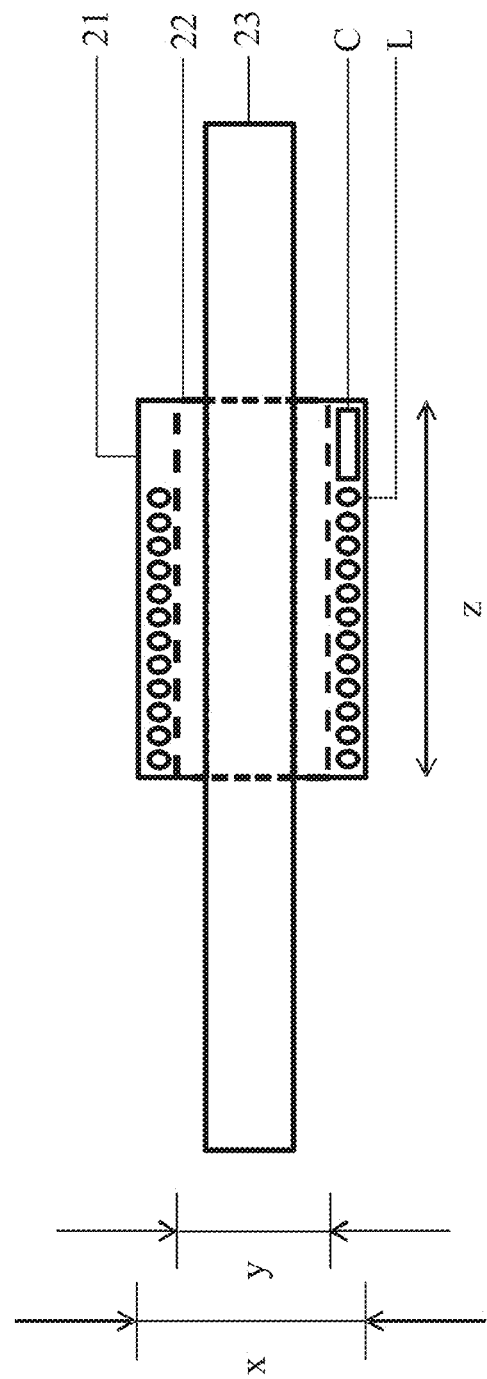

As shown in FIGS. 2a, 2b, and 2c the electronic tag can be comprised of a coil L, which is connected to a capacitor C (shown schematically). Referring to FIG. 2a, the coil L and capacitor C can be enclosed in a cylindrical housing 21 made of non-conductive material, such as plastic, with a cylindrical-shaped cavity on the inside 22. Both the coil L and the cylindrical housing 21, in which the coil is enclosed, may encircle the source guide transport path (defined by a said source guide). The cylindrical housing 21 can, for example, have an outer diameter x, preferably in the range of 3-7 mm, and an inner diameter y, preferably in the range of 2-4 mm, with x being larger than y. Both outer diameter x as well as inner diameter y are measured in a direction perpendicular to the central axis of the cylindrical housing 21. The cylindrical housing 21 has a length z, which is preferably 4-10 mm, measured in a direction parallel with the central axis. It will be appreciated that other x, y, z dimensions can be used as well.

In this example, a section of an applicator source guide 23 is present in the cylindrical housing opening 22, allowing the passage of a transport means 8 (not shown in FIG. 2a, 2c) through the electronic tag.

In some embodiments, the cylindrical housing is hermetically sealed, thus protecting the coil L and capacitor C from outside influences. In some examples, the cylindrical housing 21 may also be made of a material that is configured to be sterilised after use. This enables the electronic tags to be used multiple times. In addition, the sterilisation process can, for example, be readily executed using (standard) medical sterilisation equipment.

FIG. 2c shows a horizontal cross-section along the line II-II' of the electronic tag shown in FIG. 2a. The cross-section shows the cylindrical housing 21 with the hermetically sealed capacitor C and coil L enclosed inside. The applicator source guide 3 runs through the cylindrical cavity 22.

Figure 3:
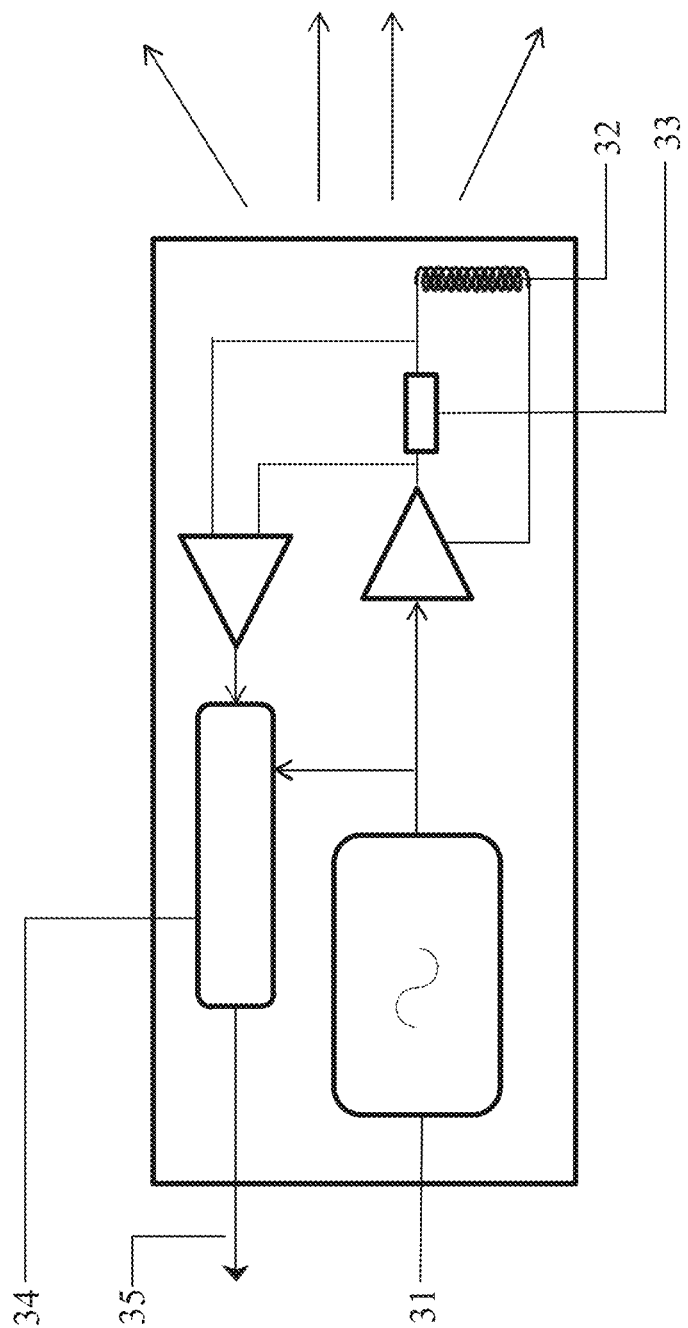
FIG. 3 is an example schematic view of a detector, consistent with disclosed embodiments.

FIG. 3 shows a schematic view of a non-limiting example of an electromagnetic field generator with detector.

The electromagnetic field generator may be powered by an AC power source 31. The power source 31 may be connected to the coil 32 and a resistor 33, for generating an electromagnetic field, and to the detector 34 which may be used to detect variations in the electromagnetic field. The detector 34 may have an external exit or signal output port 35, which may be used to communicatively connect it with a said processor or respective afterloader. The detector may contain a memory for storing the collected data and the information derived from the calibration sequence. In addition, the detector may contain a signal-conditioning unit or a signal converter to convert the signal from the electronic tag to a signal suitable for further digital processing.

Referring to FIG. 1, during use, the detector 6 may generate an electromagnetic field 7, for example, an electromagnetic field with a frequency that sweeps from 90 to 310 kHz, which field can be, in essence, directed at electronic tags 4 to be monitored. In response to receiving the signal, each electronic tag may transmit a signal at its resonance frequency, $f_r$, or—in other words—absorb or attenuate the field at that frequency, $f_r$ (for example 105 kHz), which may be perceived by the detector 6 as an increased electromagnetic load. Thus, the detector can detect resonance frequencies of the various tags 4 that are in the EM field 7.

The detector 6 can be configured to generate a detection signal upon detecting a change in a detected tag resonance frequency. Alternatively, for example, the processor K can be configured to process detection information or data provided by the detector, for detecting a change in a detected tag resonance frequency. Particularly, during operation such a change may be associated with a said transport means 8 passing the tag 4 (thereby causing a change in the resonance frequency, by EM cooperation).

It will be appreciated that various electromagnetic fields are feasible, depending e.g. on the configuration of the electronic tag 4 to be monitored. It is also contemplated to apply a dedicated noise signal, which contains all frequencies between e.g. 90 and 301 kHz, or a different frequency band (e.g., at least a frequency band that includes all frequencies of interest, regarding electronic tags 4 to be monitored).

In an operational phase, at least part of transport means 8 (for example holding a capsule containing a radioactive source S or dummy source at a distal end), can be dispensed from the afterloader 1 and guided through the e.g. transfer tube 2 and coupling 5 to the applicator 3. Movement of the transport means 8 is preferably controlled by a said controller K. Also, the movement can be monitored using the electronic tags 4.

In this example, the distal end of the transport means 8 (for example, having a capsule optionally holding the radioactive source S, or dummy source) may be configured to detune a said tag resonance frequency, $f_r$. To this aim, for example, at least the distal end of the transport means 8 may include or be made of a metal or a dielectric material capable of causing the frequency shift.

During operation, as the distal end of the transport means 8 passes a said electronic tag 4, the tag's resonance frequency detunes to a slightly different frequency, for example, from 105 kHz to 103 kHz. This may be caused by EM cooperation, for example, by a changed coil inductance (in an inductive system) or by a changed capacitance (in a capacitive system). The de-tuning may be detected by the detector 6 or controller K.

In some embodiments, the controller K generates a verification signal upon the detection of the passing of the distal end of the transport means 8 with respect to an electronic tag 4. Such a verification signal can be used to signal an operator whether or not the transport means 8 has passed a tag 4 associated with a correct guide 2 and applicator 3.

In an embodiment, the controller K is configured to use a detected tag position as a reference point, for example, a starting point of a desired subsequent source trajectory leading to a target area (that is, towards one or more distal treatment or dwelling positions, viewed along a source path). For example, the controller K can use information regarding detection of a tag in a treatment plan. Also, in an embodiment, the controller K can be configured to take action in case the verification signal significantly deviates from a desired or expected signal, which may be the case when the distal end of the transport means 8 has entered the wrong guide or in case the transport means 8 has a significantly different length than an expected length. A said controller action can be, for example, retracting the transport means 8 and/or generating an alarm signal or alarm.

In some embodiments, the system may be configured to be auto-calibrating, since the resonance frequency of an electronic tag may slightly differ in various locations due to environmental conditions, for example, humidity and temperature. In the auto-calibration operation (e.g. step 109 in FIG. 4), the applicator source guide does not have to be provided with a radioactive source. The detector 6 may provide an electromagnetic field 7, which is received by the electronic tag 4, which responds with its resonance frequency. Due to the environmental conditions, this may, for example, be 104.3 kHz instead of 105 kHz. This alternative resonance frequency of the electronic tag 4, without a radioactive or dummy source present, may be subsequently stored by the detector 6 as the new resonance frequency of the electronic tag 4.

Figure 4:
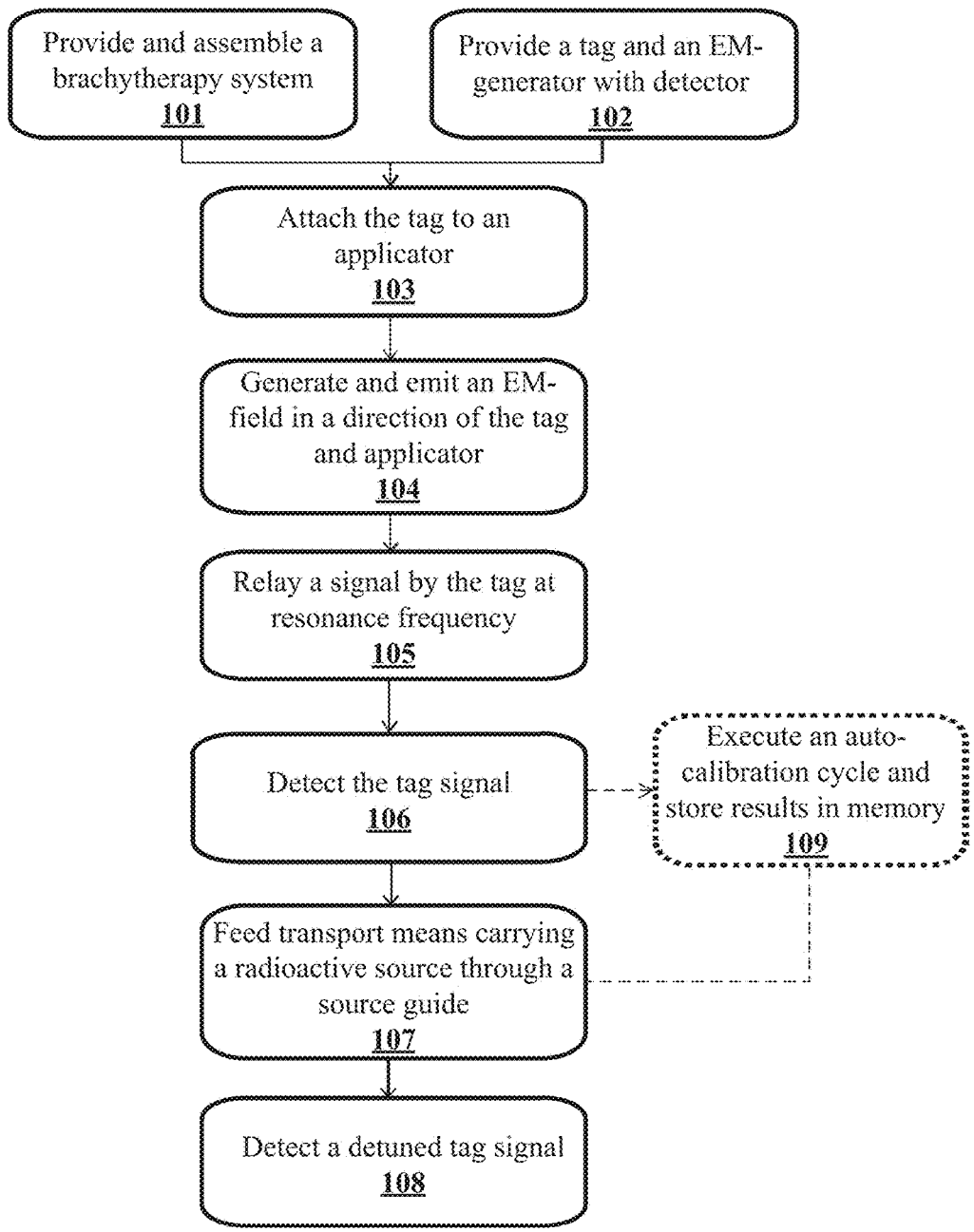
FIG. 4 is an example flow chart of a method, consistent with disclosed embodiments.

FIG. 4 shows a flow chart of a method for guiding a radioactive source transport means through a source guide, for performing brachytherapy. The method can include the following steps 101-109:
- a step 101 of providing and assembling a brachytherapy system;
- a step 102 of providing a tag and an EM-generator with detector;
- a step 103 of attaching the tag to an applicator;
- a step 104 of generating and emitting an EM-field in a direction of the tag and applicator;
- a step 105 of the tag relaying a signal at resonance frequency;
- a step 106 of detecting the tag signal;
- a step 107 of feeding transport means carrying a radioactive source through a source guide;
- a step 108 of detecting a detuned tag signal;
- and optionally a step 109 of executing an auto-calibration cycle and storing results in (external) memory.

In a first step 101, a brachytherapy system, comprised of at least an afterloader, one or more source guide transfer tubes, an optional source guide transfer tube-applicator coupling and an applicator with at least one source guide, is set up to form an uninterrupted connection between the afterloader and the applicator through which a radioactive source transport means can be guided.

In step 102, one or more electronic tags and an electromagnetic field generator with detector are provided for the system.

In step 103, the electronic tag may be attached to the applicator source guide, which is performed for example by sliding it over the applicator and connecting it by means of a clamp. The electronic tag can be fastened on various positions on the applicator. This step is optional when using applicator source guides with integrated electronic tags.

In step 104, the electromagnetic field generator generates an electromagnetic field substantially in the direction of each electronic tag 4, thus inducing a signal from the electronic tags at their resonance frequencies. In some embodiments, the various electronic tags 4 have different resonance frequencies.

The resonance frequency signal provided by the electronic tag (step 105), for example, 105 kHz, may be detected by the detector (step 106) and, after transformation, provides identification information on the electronic tag (i.e. being the tag with that specific resonance frequency).

In step 107, a transport means 8 carrying a radioactive source S, is released from the afterloader. In some embodiments, the transport means 8 may be guided from the afterloader 1 via a first source guide 2 into the applicator 3. In case the correct path is followed, the transport means 8 will pass the respective tags 4 that are associated with the source guide 2 and subsequent applicator 3. The passing is monitored by the controller K based on the resonance frequency detection of the tags resonance frequencies.

As the transport means 8 passes through each electronic tag 4, it detunes the resonance frequency of that electronic tag 4, resulting in a slight change (e.g. increase or decrease) in the resonance frequency of the electronic tag 4, which is detected by the detector and controller K. In an embodiment, the controller K can use the detected tag position as a reference point or starting point in a treatment plan (the plan, for example, including a number of source dwelling positions, tissue treatment positions, distributed over along a source path viewed from the position of the electronic tag).

The controller K may automatically abort further movement of the transport means 8 in case the detection of the passing of the transport means 8 (passing a said electronic tag 4) significantly deviates from expected or desired (e.g., predetermined) passing, or in case the wrong tag is detected (for example in case of entering the wrong channel). In that case, the controller K may immediately retract the transport means 8 into the housing of the applicator in case the controller K finds that the detection of the passing of the transport means 8 (passing a said tag 4) deviates from an expected or desired (e.g. predetermined) passing of that transport means.

It should also be observed that the deviation can include a situation in which no passing of the transport means 8 is detected, wherein the transport means 8 was expected to pass a certain tag 4.

In step 108, the detector receives the detuned signal. As such, the detector (e.g., controller K) can confirm that the transport means carrying the radioactive source has entered the correct source guide 2 and the correct applicator 3.

When using a system comprising multiple source guides, the detection information can also be used to ascertain that the transport means carrying the radioactive source has entered the correct channel. This provides a relatively easy control mechanism as a safeguard. Also, the control mechanism may be automated, which would provide an automatic safeguard. As follows from the above, the safeguard may comprise a warning signal or an automatic withdrawal of the transport means 8 carrying the radioactive source if the system detects that it has entered the wrong channel. System (e.g., control mechanism) may also provide both a warning signal and a simultaneous automatic withdrawal.

In addition, entry of the transport means 8 into the applicator source guide can be detected. This has the advantage that the system can support localisation of the source guide in the applicator and provide accurate information on the location at the moment the transport means 8 carrying the source S has entered the applicator source guide.

The method may, as optional step 109, also comprise auto-calibration of the system before feeding a radioactive source from the afterloader to the system. The results may be stored in an (external) memory. The optional method step provides several advantages. First of all, executing an auto-calibration step may provide information on any errors in the system. These errors, if any, can be corrected before application of the radioactive source. Furthermore, auto-calibrating the system ensures that the system is adapted to the present environmental conditions in order to attain a correct performance for those conditions.

Combining the auto-calibration step with the storage of the auto-calibration data may provide an additional advantage. Over time, the calibration data from any auto-calibration step may be compared to the stored data to provide information on the functionality of the system.

From the above it follows that the system can be used to determine a point of reference for the treatment, the point of reference being a point along a source path, remote from the afterloader. In this way, the point of reference (e.g., defined by a tag location) can be brought relatively close to the target area. It follows that accurate treatment can be achieved, as well as verification of correct channel entry, preferably in an automated manner. In this way, human error can be reduced or eliminated. Also, problems relating to source guides, such as snaking, kinks in bends, irregularities in length of tubes, et cetera, can be detected.

While specific embodiments have been described above, it will be appreciated that embodiments may be practiced otherwise than as described. The descriptions above are intended to be illustrative, not limiting. Thus, it will be apparent to one skilled in the art that modifications may be made to the embodiments as described in the foregoing without departing from the scope of the claims set out below.

For example, a said transport means can be configured in various ways. It can, for example, also be called a "transport structure" or "transport system". It can be a flexible wire or similar structure.

The source guide configured for guiding a radioactive source transport means, can include various types of guides, for example a transfer tube, an applicator of a different guide, as will be appreciated by the skilled person. The guide can, for example, be configured to conduct or deliver a source.

In an embodiment, the tag can have a cylindrical shape, for example, such that it can be placed over an applicator or tube or other source guide. In another option, the electronic tag 4 may be preassembled.

The invention claimed is:

1. A system for transporting a radioactive source used for brachytherapy, the system comprising:
   a source guide configured to guide a source transport configured to hold the radioactive source and to transport the radioactive source from a first position to a second position, wherein the source guide includes at least one electronic tag;
   a detector configured to detect a frequency signal generated by the at least one electronic tag, wherein the frequency signal varies when the source transport holding the radioactive source is proximate to the at least one electronic tag as the radioactive source is transported from the first position to the second position; and
   a controller configured to receive the frequency signal from the detector and determine a path of the source transport based on the frequency signal.

2. The system of claim 1, wherein the at least one electronic tag includes an electronic circuit having a coil that encloses a source guide path.

3. The system of claim 1, wherein the at least one electronic tag is a passive electronic tag that is configured to absorb less than all of a broadband radiofrequency signal at a specific frequency, wherein the detected frequency signal is indicative of the specific frequency.

4. The system of claim 3, wherein the specific frequency is a resonance frequency of an LC-circuit.

5. The system of claim 4, wherein the resonance frequency varies based on a presence of the source transport proximate to the electronic tag.

6. The system of claim 1, wherein the detector is a tag-reader configured to read identification information provided by the electronic tag.

7. The system of claim 1, wherein the detector is configured to automatically calibrate itself based on the frequency signal detected in absence of the source transport proximate to the at least one electronic tag.

8. The system of claim 1, wherein the detector is integrated in an afterloader configured to deliver the radioactive source to the source guide.

9. The system of claim 1, wherein the at least one electronic tag includes a detectable identification code.

10. The system of claim 1, wherein the at least one electronic tag is integrated in a closed housing, wherein the closed housing is suitable to be sterilised.

11. The system of claim 1, wherein the at least one electronic tag is attached to the source guide.

12. The system of claim 1, wherein the at least one electronic tag is an integral part of the source guide.

13. The system of claim 1, wherein the controller determines the path of the source transport by associating a location of the source transport with a location of the at least one electronic tag upon detection of a variation in the frequency signal.

14. The system of claim 1, wherein the controller is configured to reposition the source transport if the determined path differs from a programmed path of the source transport.

15. The system of claim 14, wherein the controller is configured to reposition the source transport based on a location of the at least one electronic tag.

16. The system of claim 14, wherein the controller is configured to retract the source transport out of the source guide.

17. A method for transporting a radioactive source used for brachytherapy, the method including:
    detecting a frequency signal generated by at least one electronic tag associated with a source guide configured to guide a source transport, wherein:
        the source transport is configured to hold the radioactive source and to transport the radioactive source from a first position to a second position, and
        the frequency signal varies when the source transport holding the radioactive source is proximate to the at least one electronic tag as the radioactive source is transported from the first position to the second position; and
    determining a path of the source transport based on the frequency signal.

18. The method of claim 17, further including detecting identification information from the at least one electronic tag.

19. The method of claim 17, further including automatically calibrating a detector based on the frequency signal detected in absence of the source transport proximate to the at least one electronic tag.

20. The method of claim 17, wherein the at least one electronic tag includes an LC circuit having a resonant frequency, wherein the detected frequency signal is indicative of the resonant frequency.

21. The method of claim 17, wherein the path of the source transport is determined by associating a location of the source transport with a location of the at least one electronic tag upon detection of a variation in the frequency signal.

22. The method of claim 17, further including repositioning the source transport if the determined path differs from a programmed path of the source transport.

* * * * *